(12) United States Patent
Andersson et al.

(10) Patent No.: US 9,668,621 B2
(45) Date of Patent: *Jun. 6, 2017

(54) STACK OF FOLDED WEB MATERIAL FOR HYGIENE PRODUCTS

(71) Applicant: SCA HYGIENE PRODUCTS AB, Gothenburg (SE)

(72) Inventors: Anders Andersson, Stenungsund (SE); Mattias Bengtsson, Gothenburg (SE); Bjorn Larsson, Gothenburg (SE); Inger Andersson, Varberg (SE)

(73) Assignee: SCA HYGIENE PRODUCTS AB, Gothenburg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/653,602

(22) PCT Filed: Dec. 19, 2012

(86) PCT No.: PCT/SE2012/051438
§ 371 (c)(1),
(2) Date: Jun. 18, 2015

(87) PCT Pub. No.: WO2014/098669
PCT Pub. Date: Jun. 26, 2014

(65) Prior Publication Data
US 2015/0327733 A1 Nov. 19, 2015

(51) Int. Cl.
*B32B 3/00* (2006.01)
*A47K 10/16* (2006.01)
(Continued)

(52) U.S. Cl.
CPC ............ *A47K 10/16* (2013.01); *A47K 10/34* (2013.01); *A47K 10/42* (2013.01); *A61F 13/539* (2013.01);
(Continued)

(58) Field of Classification Search
CPC ........... Y10T 428/15; Y10T 428/24231; Y10T 428/24793; A47K 10/16
See application file for complete search history.

(56) References Cited

U.S. PATENT DOCUMENTS 2,780,352 A 2/1957 Schroeder
4,725,469 A 2/1988 Summerfield
(Continued)

FOREIGN PATENT DOCUMENTS

DE 69626755 T2 3/2004
EP 0 779 053 B1 6/1997
(Continued)

OTHER PUBLICATIONS

International Search Report (PCT/ISA/210) mailed on Sep. 3, 2013, by the Swedish Patent Office as the International Searching Authority for International Application No. PCT/SE2012/051438.
(Continued)

*Primary Examiner* — Alexander Thomas
(74) *Attorney, Agent, or Firm* — Buchanan Ingersoll & Rooney P.C.

(57) ABSTRACT

A stack of folded web material for hygiene products, such as paper or nonwoven products, said stack including: at least two webs, the webs including: a first web divided into individual sheets by means of lines of weakness; and a second web divided into individual sheets by means of lines of weakness; said first and second webs being interfolded with one another so as to form said stack; and wherein the first web and the second web are arranged in said stack such that the lines of weakness of the first web and the lines of weakness of the second web are offset with respect to one another along the webs; each line of weakness having a separation strength, being the force required to separate an individual sheet from the web along said line of weakness.

25 Claims, 10 Drawing Sheets

(51) Int. Cl.
| | |
|---|---|
| *B32B 3/02* | (2006.01) |
| *B32B 7/14* | (2006.01) |
| *B32B 5/26* | (2006.01) |
| *B32B 5/02* | (2006.01) |
| *B32B 29/00* | (2006.01) |
| *B32B 3/06* | (2006.01) |
| *A61F 13/539* | (2006.01) |
| *A47K 10/34* | (2006.01) |
| *A47K 10/42* | (2006.01) |
| *B65H 45/24* | (2006.01) |
| *B65H 35/04* | (2006.01) |
| *B65H 37/04* | (2006.01) |

(52) U.S. Cl.
CPC .................. *B32B 3/02* (2013.01); *B32B 3/06* (2013.01); *B32B 5/022* (2013.01); *B32B 5/26* (2013.01); *B32B 7/14* (2013.01); *B32B 29/005* (2013.01); *B65H 35/04* (2013.01); *B65H 37/04* (2013.01); *B65H 45/24* (2013.01); *A47K 2010/428* (2013.01); *A61F 2013/53908* (2013.01); *A61F 2013/53983* (2013.01); *B32B 2555/00* (2013.01); *B65H 2601/31* (2013.01); *B65H 2701/1924* (2013.01); *Y10T 428/15* (2015.01)

(56) References Cited

U.S. PATENT DOCUMENTS

| | | | |
|---|---|---|---|
| 6,213,346 B1 | 4/2001 | Skerrett et al. | |
| 6,286,712 B1 | 9/2001 | Craig et al. | |
| 6,315,114 B1 | 11/2001 | Keck et al. | |
| 8,389,092 B2 | 3/2013 | Andersson | |
| 8,877,313 B2 * | 11/2014 | Larsson | B65H 45/24 428/100 |
| 2010/0009826 A1 | 1/2010 | Basin et al. | |
| 2011/0129633 A1 | 6/2011 | Andersson | |
| 2011/0210137 A1 | 9/2011 | Kling | |
| 2011/0315576 A1 | 12/2011 | Rucinska et al. | |
| 2014/0110299 A1 | 4/2014 | Sporre Thorburn et al. | |
| 2014/0134376 A1 | 5/2014 | Larsson | |
| 2014/0135192 A1 | 5/2014 | Andersson et al. | |
| 2014/0209624 A1 | 7/2014 | Larsson | |
| 2014/0291186 A1 | 10/2014 | Andersoon et al. | |

FOREIGN PATENT DOCUMENTS

| | | |
|---|---|---|
| EP | 1 462 389 A1 | 9/2004 |
| FR | 2 539 726 A2 | 7/1984 |
| WO | WO96/03069 A1 | 2/1996 |
| WO | WO 00/00072 A1 | 1/2000 |
| WO | WO 2004/106192 A1 | 12/2004 |
| WO | WO 2012/007301 A1 | 1/2012 |
| WO | WO 2012/173533 A1 | 12/2012 |
| WO | WO 2013/007302 A2 | 1/2013 |
| WO | WO 2013/007303 A1 | 1/2013 |
| WO | WO 2013/029678 A1 | 3/2013 |

OTHER PUBLICATIONS

Written Opinion (PCT/ISA/237) mailed on Sep. 3, 2013, by the Swedish Patent Office as the International Searching Authority for International Application No. PCT/SE2012/051438.

International Search Report (PCT/ISA/210) mailed on Jun. 12, 2013 by the Swedish Patent Office as the International Searching Authority for International Application No. PCT/SE2012/051434.

Written Opinion (PCT/ISA/237) mailed on Jun. 12, 2013, by the Swedish Patent Office as the International Searching Authority for International Application No. PCT/SE2012/051434.

International Preliminary Report on Patentability (PCT/IPEA/408) mailed on Jan. 28, 2015, by the Finnish Patent Office as the International Preliminary Examining Authority for International Application No. PCT/SE2012/051434.

International Search Report (PCT/ISA/210) mailed on Jun. 12, 2013, by the Swedish Patent Office as the International Searching Authority for International Application No. PCT/SE2012/051436.

Written Opinion (PCT/ISA/237) mailed on Jun. 12, 2013, by the Swedish Patent Office as the International Searching Authority for International Application No. PCT/SE2012/051436.

International Preliminary Report on Patentability (PCT/IPEA/409) mailed on Apr. 10, 2015, by the Finnish Patent Office as the International Preliminary Examining Authority for International Application No. PCT/SE2012/051436.

International Search Report (PCT/ISA/210) mailed on Jun. 13, 2015, by the Swedish Patent Office as the International Searching Authority for International Application No. PCT/SE2012/051437.

Written Opinion (PCT/ISA/237) mailed on Jun. 13, 2013, by the Swedish Patent Office as the International Searching Authority for International Application No. PCT/SE2012/051437.

International Preliminary Report on Patentability (PCT/IPEA/409) mailed on Apr. 20, 2015, by the Finnish Patent Office as the International Preliminary Examining Authority for International Application No. PCT/SE2012/051437.

Tork Universal Hand Towel Zigzag Fold Soft. SCA Hygiene Products AB, 405 03 Göteborg, SE. Aug. 10, 2012. [Retrieved on Jun. 4, 2013]. Retrieved from the Internet: URL:http://www.sca-tork.com/product/SI/290158.pdf; 3 pages.

* cited by examiner

STACK OF FOLDED WEB MATERIAL FOR HYGIENE PRODUCTS

TECHNICAL FIELD

The present invention relates to a stack of folded web material for hygiene products, such as paper or nonwoven products, said stack comprising: at least two webs, the webs including: a first web divided into individual sheets by means of lines of weakness; and a second web divided into individual sheets by means of lines of weakness. Said first and second webs are interfolded with one another so as to form said stack: and wherein the first web and the second web are arranged in said stack such that the lines of weakness of the first web and the lines of weakness of the second web are offset with respect to one another along the webs.

BACKGROUND OF THE INVENTION

In the field of dispensing hygiene products from a stack or roll of hygiene products arranged in a dispenser, several possibilities of arranging the hygiene products are known.

Typically, it is desired that when a product is withdrawn from the dispenser, the next product is to be automatically positioned in a dispensing position in the dispenser such that it can easily be reached by a user. To this end, it is desired to use arrangements for ensuring that a leading end of a web material including the products is always in the right dispensing position where it can be easily grasped by a user.

In dispensers which are powered, e.g. electrically, the feeding of the leading end of the web to a dispensing position may be accomplished by a powered feeding arrangement. In manual dispensers (not powered), the feeding of the leading end should however preferably be accomplished using only the force applied by a user when pulling a product from the web material.

Stacks of interfolded hygiene products have been suggested in which two webs, each comprising connected individual hygiene products, are provided in an interfolded manner.

The individual hygiene products are defined by the two webs both being provided with weakening lines, such as perforation lines, such that the individual hygiene products are connected to one another by the weakening lines before separation into individual products by a user rupturing said weakening lines. To ensure the presentation of a leading end of a web to a user, it has been proposed to arrange the two webs in the stack such that the weakening lines of one web are offset with respect to the weakening lines of the other web.

Hence, when the stack comprising the two webs being arranged in an offset relationship is set-up in an appropriate dispenser, and a user pulls the leading individual hygiene product, a weakening line of the web containing the product will break so as to separate said hygiene product from that web, and, simultaneously, the other of the two webs will be pulled along with the product, such that a leading end of a product from the other web will now be presented to a user. Accordingly, automatic feeding may be achieved in a manual dispenser.

However, stacks comprising two interfolded webs as described in the above are also suitable for use in powered dispensers.

WO00/00072 describes an example of a stack of interfolded products in accordance with the above.

However, the use of a stack consisting of at least two separate webs running in parallel, may also invoke some problems.

In a dispenser, the web material will generally run from a storage space for containing the stack of folded material, to a dispensing opening. Hence, the dispenser will define a web path along which unfolded web material runs from said storage space to said dispensing opening.

In particular when it is desired to enable storing of a relatively large amount of web material in the dispenser, it has been proposed to arrange the storage space and the web path such that the web material is fed from the top of the stack.

Generally, along said web path, the web material may be supported by various means such as rollers, nips etc. Some of those means could be efficient to urge the two webs of the web material together.

For initial set-up of a web of material to be dispensed, the stack must be positioned in the storage space of the dispenser, and a leading end of the web material must be threaded along the web path to the dispensing opening. Such threading might involve pulling the web through nips or over rollers of various kinds, and might sometimes be rather difficult to perform. It has been realized that threading such dispensers using a stack comprising at least two separate webs might be perceived as extra difficult, as it must be ensured that both webs are correctly introduced, and with a maintained offset relationship between the webs. Moreover, if an unintentional web breakage occurs somewhere along the web path, another threading of web material must be performed to re-set the web material in the dispenser.

For correct feeding of the web material from the dispenser, it is necessary that the offset relationship between the two webs is maintained. However, there is a risk that this relationship is disturbed along the web path, in other words, that the feeding of the two webs, respectively, becomes asynchronous. This in turn might lead to less than optimal dispensing of sheets from the dispenser. This problem has been found to be particularly manifest in dispensers where the web is to be fed from the top of the stack of material, presumably because of the action of gravity. Also, since the asynchronisation between the webs may increase in magnitude during continued dispensing of the web material, it becomes particularly pronounced during uninterrupted dispensing of relatively long lengths of web material, such as when using large stacks and/or several interconnected stacks for forming long uninterrupted web lengths. At the same time, uninterrupted dispensing is desired since it lessens the need for maintenance of the dispensers.

It is the object of the invention to provide an improved stack of web material in regard of at least one of the above-mentioned aspects.

SUMMARY OF THE INVENTION

In a first aspect of the invention, the above-mentioned object is achieved by a stack of folded web material for hygiene products, such as paper or nonwoven products, said stack comprising: at least two webs, the webs including: a first web divided into individual sheets by means of lines of weakness; and a second web divided into individual sheets by means of lines of weakness, said first and second webs being interfolded with one another so as to form said stack. The first web and the second web are arranged in said stack such that the lines of weakness of the first web and the lines of weakness of the second web are offset with respect to one another along the webs.

With "lines of weakness" is meant herein lines which are weaker than the web material in general, and which are intended to separate the web material into separate sheets. The lines of weakness may preferably be perforation lines.

As is per se conventional in the art, each line of weakness will have a separation strength, being the force required to separate an individual sheet from the web along said line of weakness In accordance with said first aspect of the invention, the first web and the second web are joined to each other at a plurality of joints forming a plurality of individual sheet interconnections in said stack. Each "individual sheet interconnection" is formed by the joint or joints connecting an individual sheet of the first web with an individual sheet of the second web.

Hence, an individual sheet interconnection between an individual sheet of the first web and an individual sheet of the second web may comprise one or more joints.

Each individual sheet interconnection will have a separation strength, being the force required to separate the two individual sheets of the first and the second web respectively from each other, such that the joint or joints forming said individual sheet interconnection are broken.

In accordance with said first aspect, the separation strength of the individual sheet interconnections is less than the separation strength of the lines of weakness in said stack.

In accordance with the above, it is suggested that individual sheet interconnections joining the first and the second web are distributed along the two webs of the stack.

The individual sheet interconnections are intended to ensure that the relationship between the two webs is maintained also during threading and/or along the web path travelled in a dispenser, whereby the above-mentioned object is achieved.

However, a disadvantage with interconnecting the two webs together may be that a user pulling a leading end of one of the webs risks being served more than one single individual sheet. In other words, if the individual sheet interconnections are made too strong, a user pulling an individual sheet from a dispenser would risk receiving a number of sheets, from both webs, said sheets being interconnected by the individual sheet interconnections.

It has now been realised that to avoid the presumed disadvantages with joining the two webs, while maintaining the advantages, the separation strength of the individual sheet interconnections should be determined in relation to the separation strength of the lines of weakness. If the separation strength of the individual sheet interconnections is less than the separation strength of the lines of weakness, the problem with sheets from both webs being served at the same time may be avoided.

The separation strength required to ensure that the two web sections are held together and do not become asynchronous will depend on several circumstances, such as the frequency of the individual sheet interconnections along the web, the design of the dispenser in which the stack is to be used, etc.

However, it has been realised that advantageously the separation strength of the individual sheet interconnections may be relatively small, preferably less than 0.1 times the separation strength of the lines of weakness, more preferred less than 0.05 times. Relatively weak sheet interconnections are advantageous in that they will hardly be perceivable by a user, and yet provide the desired advantages.

The actual force measure of the separation strength will depend on the forces involved in the dispensing system as a whole—the strength of the web material, the pulling force selected for the dispenser, as well as of course the separation strength of the weakening lines.

In a preferred embodiment, the separation strength of the individual sheet interconnections is in the range 0.01-5 N, preferably 0.01-1 N.

Again, in a preferred embodiment, advantageously the separation strength of the individual sheet interconnections is greater than 0.01 N, preferably greater than 0.05 N, most preferred greater than 0.10 N.

A preferred separation strength of the lines of weakness may be in the range 1-30 N, preferably 3-20 N, most preferred 3-10 N.

All of the above preferred embodiments are particularly suitable for a stack of sheets with a web quality being suitable for hand towels and to be used in a dispenser, in particular a dispenser arranged for feeding of web material from the top of the stack.

At present, the preferred method for forming said joints is by gluing. This method is easily controllable so as to achieve the necessary separation strengths of the individual sheet interconnections.

However, it is envisaged that the joints forming said individual sheet interconnections could be created using various method for web material interconnections as known in the art, including mechanical bonding and/or chemical bonding. Mechanical bonding could be accomplished e.g. by embossing, edge embossing, and/or needling. Chemical bonding could include formation of hydrogen bonds. Mechanical and chemical bonding could also occur simultaneously e.g. when gluing.

The present inventors have realised, that a suitable separation strength may be achieved by the joints of said individual sheet interconnections being formed by adhesive, and in particular by that, in each individual sheet interconnection, the amount of adhesive of the total joint or joints of said individual sheet interconnection is in the range 0.0001-1 mg, when calculated with a dry content of 100%.

An adhesive with a dry content of 100% is for example a hot melt. When other types of adhesives are used, the preferred amount of that adhesive should be adjusted with regard to the dry content thereof.

Generally, each web defines a web material surface being delimited by the longitudinal outer edges of the web. When folded into a stack, the web material surfaces form panels extending between consecutive folding lines, said panels being arranged in a superposed relationship to form a stack extending between a bottom panel and a top panel. The longitudinal edges of the webs will form two opposite sides of the stack, and the fold lines will form the other two opposite sides of the stack.

The joints may be formed so as to join the web material surface of the first web with the web material surface of the second web.

Alternatively, or in addition to the joining of the web material surfaces, the joints may be formed so as to join the longitudinal edges of the first web with the longitudinal edges of the second web.

The joints may be provided in any suitable pattern or shape. The pattern may be intermittent or continuous.

For example, the joints may advantageously be formed from adhesive being applied in a dot pattern.

Moreover, joints may be provided in a decorative pattern, optionally forming decorative elements such as leaves. Also, when adhesive is used for forming the joints, the adhesive may be coloured in one or several colours so as to obtain a decorative effect.

In one embodiment, each individual sheet interconnection comprises one joint only, said joint consisting of one dot of adhesive, preferably said dot of adhesive comprises amount of adhesive between 0.0001 mg and 1 mg, as calculated with a dry content of 100%.

Advantageously, said joint consisting of one dot may be applied so as to join the web material surfaces of the first and second webs.

When the joints are arranged so as to interconnect the longitudinal edges of the first web with the longitudinal edges of the second web, the joints may be applied in an intermittent pattern as seen from a side of the stack comprising said longitudinal edges. Each joint may be formed by an amount of adhesive in the range 0.0001-1 mg.

When the joints are arranged so as to interconnect the longitudinal edges of the first web with the longitudinal edges of the second web, the joints may alternatively be applied in a continuous line pattern, as seen from a side of the bundle comprising said longitudinal edges, preferably said continuous line pattern has a width in the range 0.5-10 mm.

Depending on the distribution of the individual sheet interconnections, and the size of the sack, the sum of all of the individual sheet interconnections of said stack may comprise an amount of adhesive which varies considerably, e.g. in the range 0.2 to 250 mg.

A stack could advantageously comprise about 100 to 1000 individual sheets.

Advantageously, the lines of weakness in said first web are regularly distributed throughout the web, the distance between consecutive lines of weakness corresponding to the length of the individual sheets.

Advantageously, the lines of weakness in said second web is regularly distributed throughout the second web, the distance between consecutive lines of weaknesses corresponding to the length of the individual sheets.

Preferably, the distance between consecutive lines of weakness in the first web is equal to the distance between consecutive lines of weakness in the second web. In other words, the length of the sheets of the first web is equal to the length of the sheets of the second web.

The above features regarding the positions of the lines of weakness and the length of the sheets are to be understood as referring to the majority of the sheet lengths in the stack, e.g. more than 80% or more of the lengths. There could be exceptions to these features, in particular at the ends of the stack where e.g. an occasional shorter sheet length could be used.

Preferably, and as is conventional, substantially all of the lines of weakness in the stack has the same separation strength.

Preferably, substantially all of the individual sheet interconnection in the stack have the same separation strength.

Advantageously, the stack is provided with a connection means for connection to another stack at at least one of the ends of said stack.

The connection means may comprise an adhesive, an adhesive pad, or a hook and loop fastener.

In one alternative, an individual sheet interconnection is provided at least on every fourth, preferably on every second, most preferred on every sheet throughout at least majority of the length of the webs in the stack, preferably at least 90% of the length of the webs in the stack.

The above configuration is believed to be efficient for ensuring that the two webs are held together during threading of a dispenser. In particular, it is robust so as to enable easy re-threading also if the web material has been unintentionally ruptured anywhere along the web material.

In another alternative, the individual sheet interconnections are distributed throughout the web such that that less than every fourth sheet of the webs are interconnected via individual sheet interconnections, preferably less than every $10^{th}$ sheet is interconnected, more preferred less than every $20^{th}$ sheet, most preferred the interconnections are provided in the range of every $20^{th}$-$100^{th}$ sheet.

The above configuration is believed to provide sufficient interconnection between the two webs so as to avoid the problems associated with asynchronisation of the two webs.

In a second aspect of the invention, there is provided a stack of folded web material for hygiene products, such as paper or nonwoven products, said stack comprising: at least two webs, the webs including: a first web divided into individual sheets by means of lines of weakness; and a second web divided into individual sheets by means of lines of weakness; said first and second webs being interfolded with one another so as to form said stack. The first web and the second web are arranged in said stack such that the lines of weakness of the first web and the lines of weakness of the second web are offset with respect to one another along the webs. The first web and the second web are joined to each other at a plurality of joints forming a plurality of individual sheet interconnections, wherein an individual sheet interconnection is formed by the joint or joints connecting an individual sheet of the first web with an individual sheet of the second web. Said joints are distributed throughout the webs, such that less than every fourth sheet of the webs are interconnected via individual sheet interconnections.

According to said second aspect, a solution to the problem with asynchronisation of the two webs during dispensing thereof is proposed.

For example, less than every $10^{th}$ sheet of each web may be interconnected via individual sheet interconnections, preferably less than every $20^{th}$ sheet, most preferred in the range between every $20^{th}$ sheet and every $100^{th}$ sheet.

When rather few sheets are interconnected, any problems with joints between the two webs being too strong, will appear relatively infrequently, and might be tolerated. If so, according to the second aspect of the invention, the separation strength of the individual sheet interconnections need not be adjusted to the separation strength of the lines of weakness.

However, the provision of relatively few individual sheet interconnections in accordance with the second aspect may naturally advantageously be combined with the relationship between separation strengths as suggested in the first aspect of the invention.

In a third aspect of the invention, there is provided a stack, comprising:

At least two webs, the webs including: a first web divided into individual sheets by means of lines of weakness; and a second web divided into individual sheets by means of lines of weakness. The first web and the second web are arranged in said compound web such that the lines of weakness of the first web and the lines of weakness of the second web are offset with respect to one another along the webs. The first web and the second web are joined to each other at a plurality of joints forming a plurality of individual sheet interconnections, wherein an individual sheet interconnection is formed by the joint or joints connecting an individual sheet of the first web with an individual sheet of the second web; and a leading portion and/or trailing portion of the webs is free from joints. Said leading and/or trailing portion of the webs instead being provided with a connection means for connection to another stack, said connection means interconnecting said first web and said second web.

In the third aspect of the invention, the leading and/or trailing end of the stack may be free from joints, since the desired interconnection between the two webs is performed by a connection means rather than via the joints.

This alternative may naturally be combined with the two above-mentioned aspects of the invention, to combine the various advantages.

The leading and/or trailing portion being free from joints may have a length of 0.2 to 1 times or more preferably 0.5 to 1 times the length of an individual sheet.

Optionally, the compound web is free from joints on at least the first 5 leading and/or trailing sheets of the first or second web.

In a fourth aspect of the invention, there is provided a stack of web material for hygiene products, such as paper or nonwoven products, comprising: at least two webs, the webs including: a first web divided into individual sheets by means of lines of weakness; and a second web divided into individual sheets by means of lines of weakness; each web defining a web material surface being delimited by longitudinal edges of the web material; wherein the first web and the second web are arranged in said compound web such that the lines of weakness of the first web and the lines of weakness of the second web are offset with respect to one another along the webs. The first web and the second web are joined to each other at a plurality of joints forming a plurality of individual sheet interconnections, wherein an individual sheet interconnection is formed by the joint or joints connecting an individual sheet of the first web with an individual sheet of the second web; and said joints are arranged to join the longitudinal edges of said first and second web.

Moreover, application of the joints to the longitudinal edges of the webs may be advantageous from a manufacturing point of view, which will be explained in more detail in the below.

In a fifth aspect of the invention, there is provided a method for producing a stack in accordance with the above of two interfolded individual web sections, such as two tissue web sections from two continuous web of material, comprising the steps of, For both webs, carrying out the following method steps in parallel:
  a) Directing the continuous web to a weakening station
  b) Weakening the continuous web so as to form weakening lines extending laterally across the continuous web at first predetermined locations, whereby individual sheets of web material are formed between consecutive weakening lines,
  c) Directing the continuous web to a cutting station:
  d) Cutting the continuous web into web sections at second predetermined locations,
  e) Folding the two web sections formed from the two separate continuous webs to a stack, such that the lines of weakness of the first web and the lines of weakness of the second web are offset with respect to one another along the webs in said stack.

The method comprising the formation of a plurality of joints between said first and said second web, the plurality of joints forming a plurality of individual sheet interconnections.

In one embodiment, the web sections each comprise a web surface delimited by longitudinal edges, and said joints are provided to the web surface so as to interconnect the first and the second web section via their respective web surface.

In this case, the joints may advantageously be applied to the web sections before interfolding the two web sections to form a stack of interfolded sheets (step e), preferably after cutting the web sections (step d) and before interfolding the web sections (step e).

The joints may suitably be applied at a joint application station, the joint application station preferably comprising an adhesive spray application unit or a hot melt applicator unit.

In another embodiment, the joints are applied to the web sections after interfolding the webs to form a stack of interfolded sheets, via at least one side of the stack formed by the longitudinal edges of the web sections.

In this case, the joints may be applied at a joint application station, the joint application station preferably comprising an adhesive spray application unit or a hot melt applicator unit.

Alternatively, in this case, the joints may be applied at a joint application station, the joint application station including a bar structure which is first provided with adhesive and then brought into contact with the stack of interfolded sheets for application of the adhesive via said at least one side of the stack.

The bar structure may optionally be smooth, such that adhesive may be provided in a continuous line to at least one side of said stack.

The bar structure may optionally be serrated, such that adhesive may be provided intermittently to at least one side of said stack.

The joints may be applied so as to interconnect the web sections substantially only at their longitudinal edges, and said bar structure may therefore be applied to the longitudinal edges of the web sections forming at least one side of said stack only.

Alternatively, the joints may be applied so as to interconnect the web sections at least partly via the web material surfaces of the web sections, and said bar structure may to this end be at least partially introduced between the web material surfaces via the sides of the stack.

For example, a serrated bar structure could be used, the bar structure having protrusions which are insertable between the panels of the stack via at least one side thereof. In this case, adhesive may be provided to the web material surfaces and possibly also on the longitudinal edges thereof, via at least one side of the stack.

In another example, a bar structure (serrated or smooth) could be used to provide adhesive only to the longitudinal edges of the webs. In this case, the bar structure would be provided with an adhesive and then pressed onto at least one side of the stack, but without becoming introduced between the panels. The result would be that glue is applied to the side of the stack only, so as to interconnect the longitudinal edges of the webs only.

Application of adhesive to the sides of the stack, to enable interconnection of the longitudinal edges of the webs only, and/or to the web surfaces of the stack might also be performed by an adhesive spray application unit, or other known joining devices. Such a spray application unit could for example be a unit having an electromagnetic nozzle.

In a sixth aspect there is provided an apparatus for producing stacks in accordance with the above, of two interfolded individual web sections, such as two tissue web sections from two continuous web of material from two continuous webs of material, comprising, for each web: a weakening station for providing weakening lines laterally across the web, a cutting station for cutting said web into an individual web section, and for both webs, a folding station for interfolding the two individual web sections into a stack.

Moreover, there is provided a joint application station for providing joints between said first individual web section and said second individual web section.

In a seventh aspect of the invention there is provided a dispenser including a housing having a storage space comprising web material in the form of a stack in accordance with the above, said dispenser having a dispensing opening for providing sheets of said web material to a user, said dispenser defining a web path, along which unfolded web material from said stack runs from said storage space to said dispensing opening, said housing and said web path being arranged such that the web is fed from the top of the stack.

In an eight aspect of the invention there is provided the use of a stack in accordance with the above in a dispenser including a housing having a storage space for comprising web material in the form of said stack.

Advantageously, the dispenser has a dispensing opening for providing sheets of said web material to a user, said dispenser defining a web path, along which unfolded web material from said stack runs from said storage space to said dispensing opening, said housing and said web path being arranged such that the web is fed from the top of the stack.

Other features and advantages as described in the above in relation to the stack of the invention may naturally also be applied to the present method, apparatus and use.

BRIEF DESCRIPTION OF THE DRAWINGS

In the following, the embodiments of the invention will be further described with reference to the exemplary drawings, wherein.

Like reference numbers denotes similar features in the respective drawings.

DETAILED DESCRIPTION OF PREFERRED EMBODIMENTS

Figure 1:
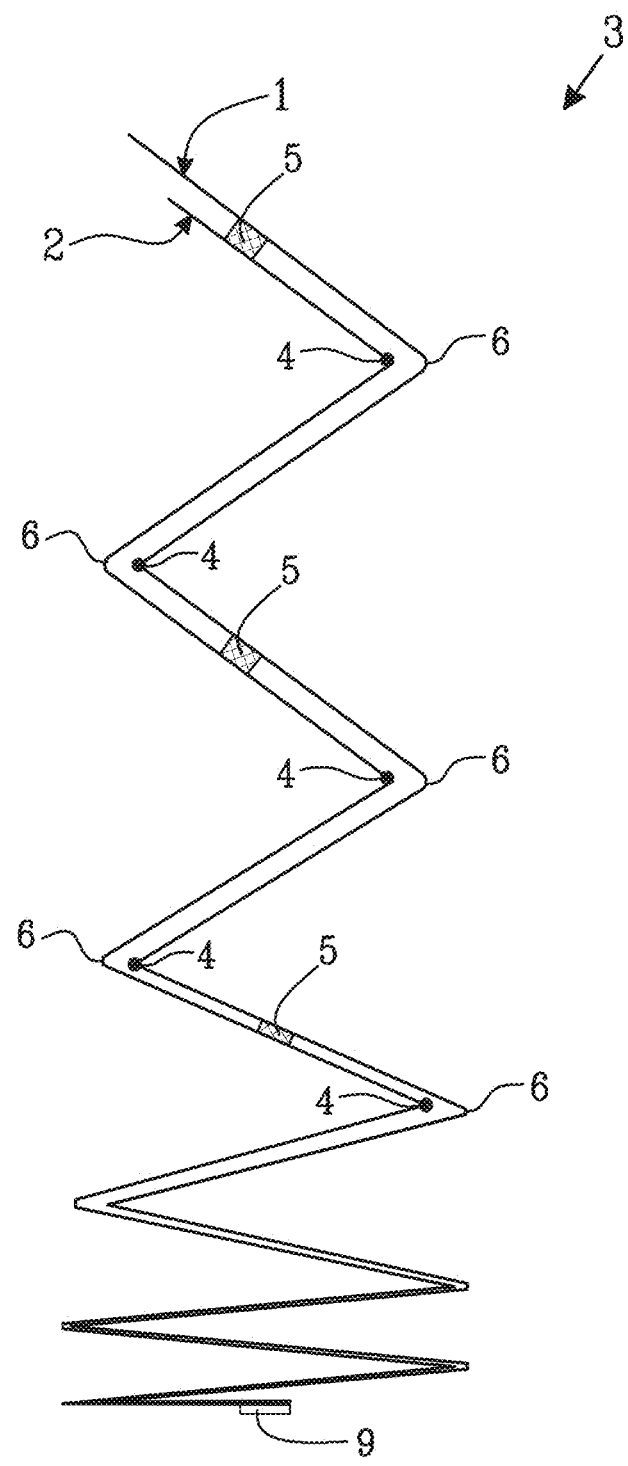
FIG. 1 illustrates an embodiment of a stack in accordance with the invention.

FIG. 1 illustrates an embodiment of stack 3 in accordance with the invention. The stack comprises a first web 1 and a second web 2.

The first and the second webs 1, 2 are folded in an accordion-like manner along fold lines 6. The distance between two consecutive fold lines 6 corresponds to the width of the stack. Hence, the webs 1, 2 are folded into panels having the stack width, and the stack 3. is constituted by said panels being arranged adjacent to one another.

Both webs 1, 2 are divided into individual sheets by means of lines of weakness 4, extending laterally across the webs. Hence, sheets of web material are formed, said sheets having a length corresponding to the distance between consecutive lines of weakness.

In the stack 3, the first and the second webs 1, 2, are arranged in relation to each other such that the lines of weakness 4 of the first web 1 and the lines of weakness 4 of the second web 2 are offset.

The first and the second webs 1,2 are joined to each other at a plurality of joints 5 forming a plurality of individual sheet interconnections.

Figure 2:
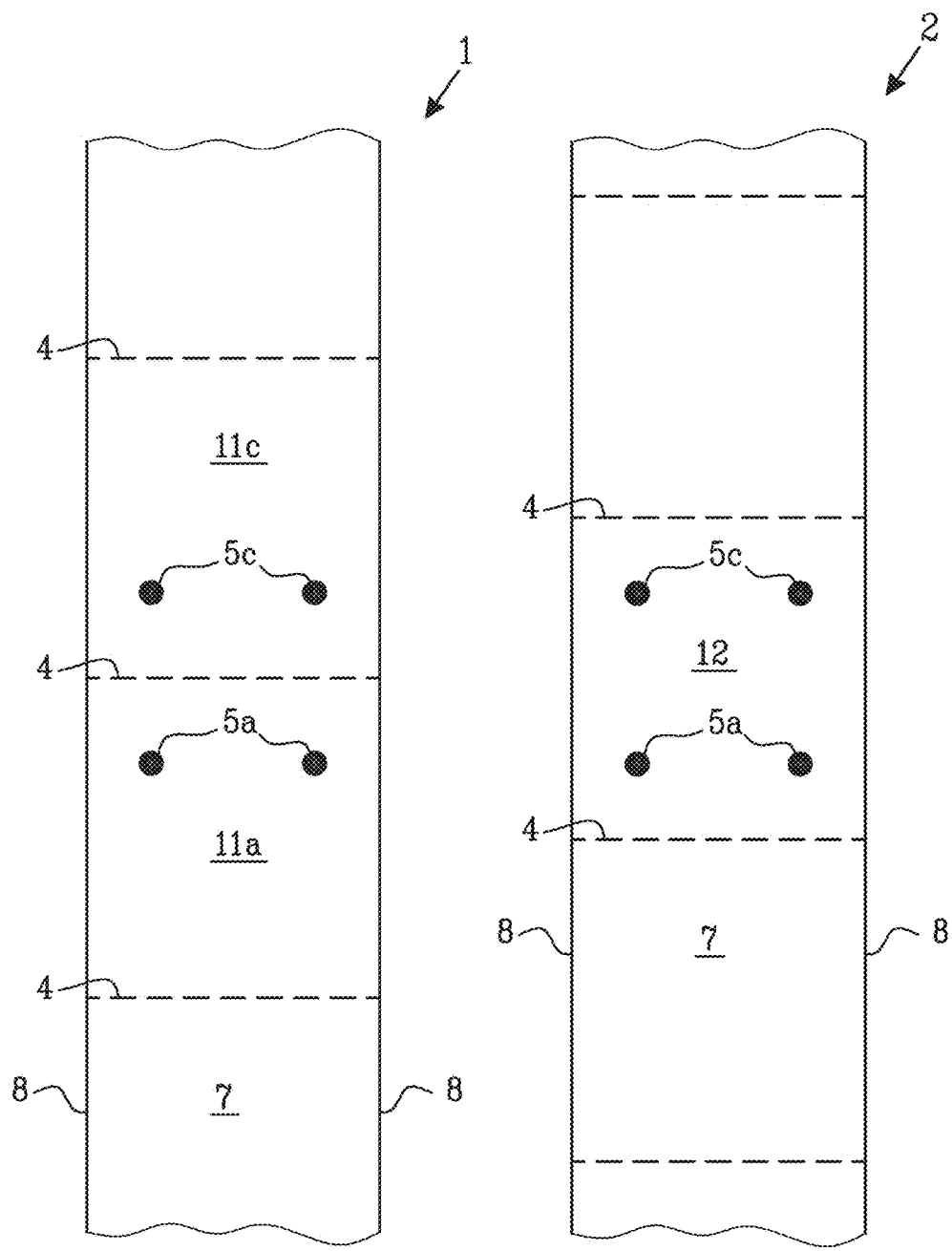
FIG. 2 illustrates the two webs in an embodiment of a stack in accordance with the invention, as unfolded and laid out side by side.

The concept of an "individual sheet interconnection" is explained in relation to FIG. 2. FIG. 2 illustrates two webs 1,2, as seen if the joints were broken and the webs displayed side by side, both webs having the web material surface 7 which is to face the other one of the webs turned upwards.

The first web 1 defines a web surface 7 extending between longitudinal edges 8. The first web 1 is provided with lateral weakening lines 4 dividing the web into individual sheets, such as sheet 11a and 11c.

10 The second web 2 likewise defines a web surface 7 extending between longitudinal edges 8. The second web is provided with weakening lines 4 dividing the web into individual sheets, such as sheet 12.

The first and second webs 1 and 2 are arranged such that the respective weakening lines 4 are offset.

The first and second webs 1 and 2 are joined together via joints 5a and 5c, interconnecting their respective web material surfaces 7.

As illustrated in FIG. 2, a first set of joints 5a will interconnect individual sheet 11a of the first web 1 with the individual sheet 12 of the second web. Hence, an individual sheet interconnection is achieved between sheet 11 a and sheet 12, by the two joints denoted 5a.

Moreover, the first and second webs 1, 2 are joined together via a second set of joints 5c. These joints 5c will interconnect the individual sheet 11c of the first web 1 with the individual sheet 12 of the second web. Hence, another individual sheet interconnection is achieved between sheet 11c and sheet 12, by the two joints denoted 5c.

A great variety of joint patterns may be envisaged. However, regardless of the pattern of the joints, the frequency thereof, etc, an individual sheet interconnection is the sum of the joints connecting two specific sheets, one from each web, with each other.

The strength of the individual sheet interconnections is to be less than the strength of the lines of weakness 4.

That this is the case may be evaluated by pulling a sheet of one of the webs adjacent an individual sheet interconnection. If the sheet may readily be separated from the web section by breaking the line of weakness without any additional tearing required to break also the individual sheet interconnection, the separation strength of the individual sheet interconnection is less strong than the separation strength of the line of weakness.

When considering strengths, and breaking of connections, it is to be noted that it is intended that the joints of the sheet interconnections shall break—not that the web material itself shall break at the sheet interconnection. Hence, the strength and type of joints used should naturally be adapted to the quality of the web in question.

When using an adhesive to form the joints of the individual sheet interconnections, the amount of adhesive will determine the strength of the joint and hence have an impact on the separation strength of the individual sheet interconnections. It has been found that an amount of adhesive in the range 0.0001-1 mg of each individual sheet interconnection may be useful for the practical circumstances involved.

Herein, adhesive amounts are discussed for an adhesive with a dry content of 100%. If adhesives with other dry contents are used, the amounts should be compensated for the different dry content.

With lines of weakness is meant herein lines which are intended to separate the web material into separate sheets.

Preferably, and as indicated in the embodiments of the illustrations, the lines of weakness may be perforation lines.

Advantageously, the perforation lines are formed by alternating bonds and slots. It has been found that a remaining bonded length being the total bond length/(total bond length +total slot length) is between 4% and 50%, preferably between 4% and 25%, most preferred between 4% and 15%, is suitable for the most relevant applications of the stack. The total bond length/(the total bond length+total slot length) may be used as an indication of the strength of the perforation line. It is desired to form perforation lines which are strong enough to enable feeding of the web material from the stack in a suitable dispenser, but which are also weak enough to enable separation of the sheets. In this context, it is known that other parameters will also influence the strength of the perforation line, such as the paper quality, and the size, shape and distribution of the slots and tabs. The above-mentioned measure may therefore be useful for guiding the person skilled in the art when selecting suitable perforation lines.

However, for determining the "separation strength" of the perforation lines, the remaining bonded length measure is inadequate, and instead the method as described hereinbelow should be used.

The methods described herein are the one used for giving the examples of suitable regions of separation strengths of weakening lines and individual sheet interconnections herein. However, since the determination of whether the separation strength of an individual sheet interconnection is less than the separation strength of a weakening line is a relative determination, it is envisaged that other methods could successfully be used for that purpose. Also, as mentioned in the above, for practical purposes the mere fact that the sheets may be withdrawn from the stack one by one, without any incidents where the sheet interconnection results in a user being provided with two interconnected sheets, indicates that the individual sheet interconnections have a weaker separation strength than the weakening lines.

Figure 3:
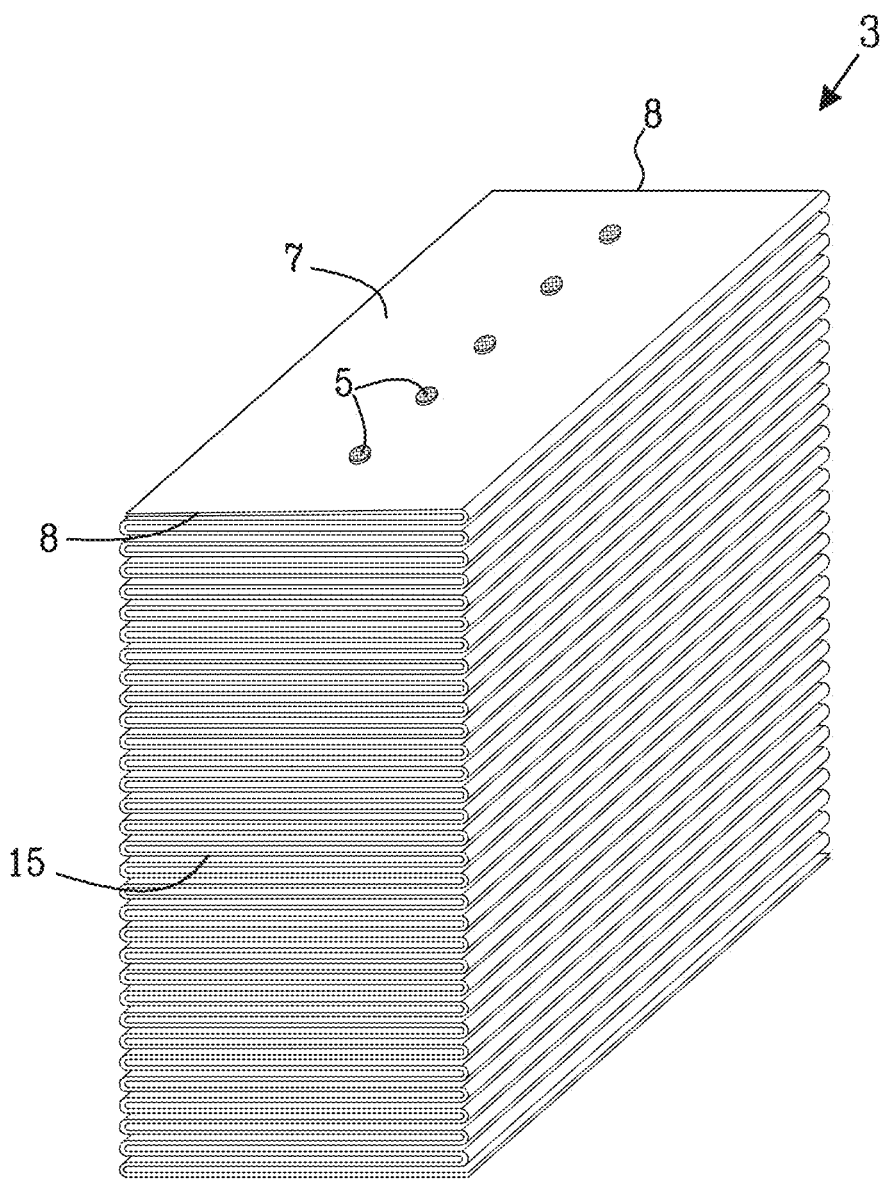
FIG. 3 illustrates another embodiment of a stack in accordance with the invention.

FIG. 3 illustrates a stack 3 of web material, where a portion of the stack is removed so as to reveal joints 5 formed in the stack. The joints 5 in this example are again interconnecting the material surfaces 7 of the webs to each other. The joints 5 could be distributed in different numbers, sizes and patterns over the panel of the stack.

Joints 5 to interconnect the material surfaces 7 of the webs, to each other may preferably be applied in the form of adhesive which is added to at least one of the webs 1, 2 before the two webs are interfolded to form a stack. The adhesive may for example be sprayed or printed onto the material surface 7.

Figure 4:
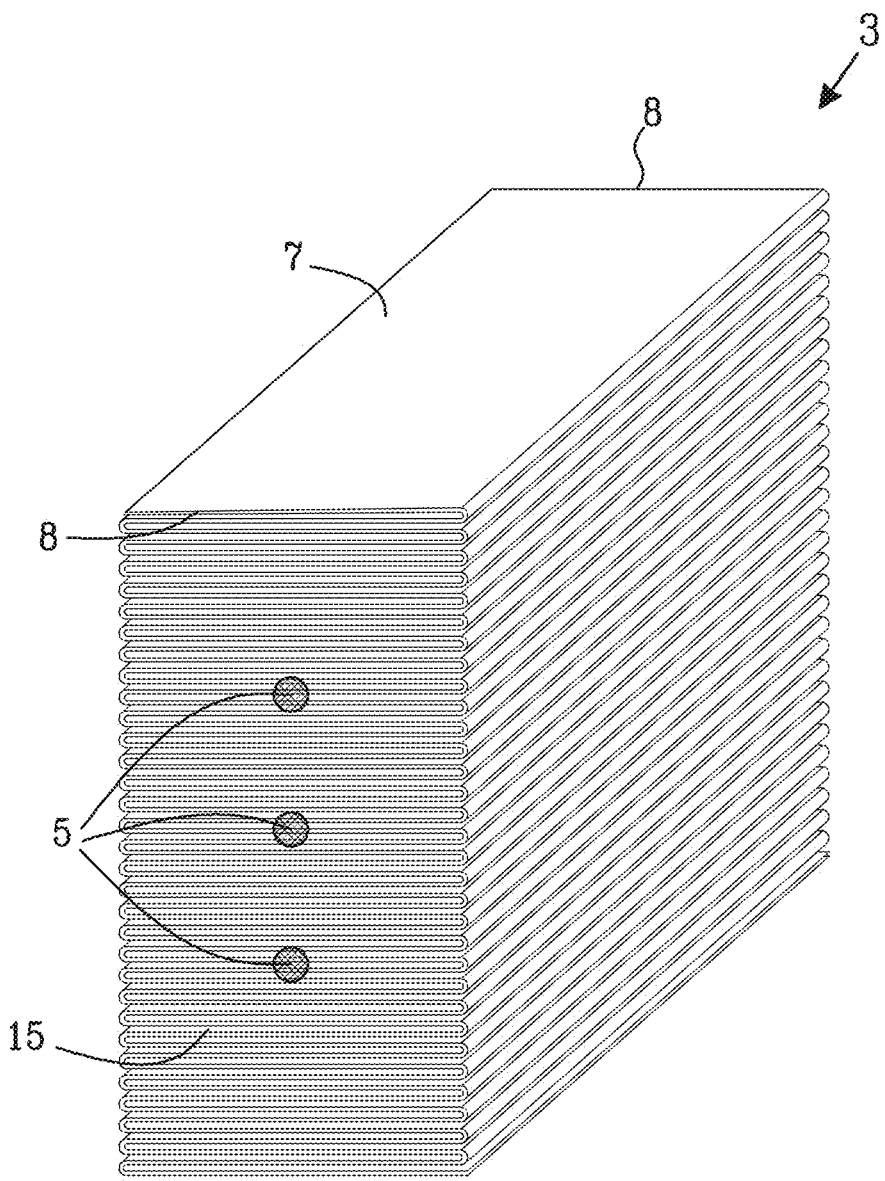
FIG. 4 illustrates yet another embodiment of a stack in accordance with the invention;.

FIG. 4 illustrates another stack 3 of web material, where the joints are not interconnecting the material surfaces 7 of the webs to each other, but instead the joints 5 are interconnecting the longitudinal edges 8 of the webs to each other. To this end, joints 5, preferably in the form of adhesive, may be applied to at least one side 15 of the stack, said side 15 comprising longitudinal edges 8 of the two webs.

The application of joints to one side 15 of the stack 3 may be performed by adding adhesive to the side 15, once the stack 3 has been created by interfolding the webs. The application of adhesive may be used by conventional methods such as spraying or printing.

Moreover, it is proposed that the application of adhesive to at least one side 15 of the stack could be made using a bar structure, either smooth or serrated.

Figure 5A:
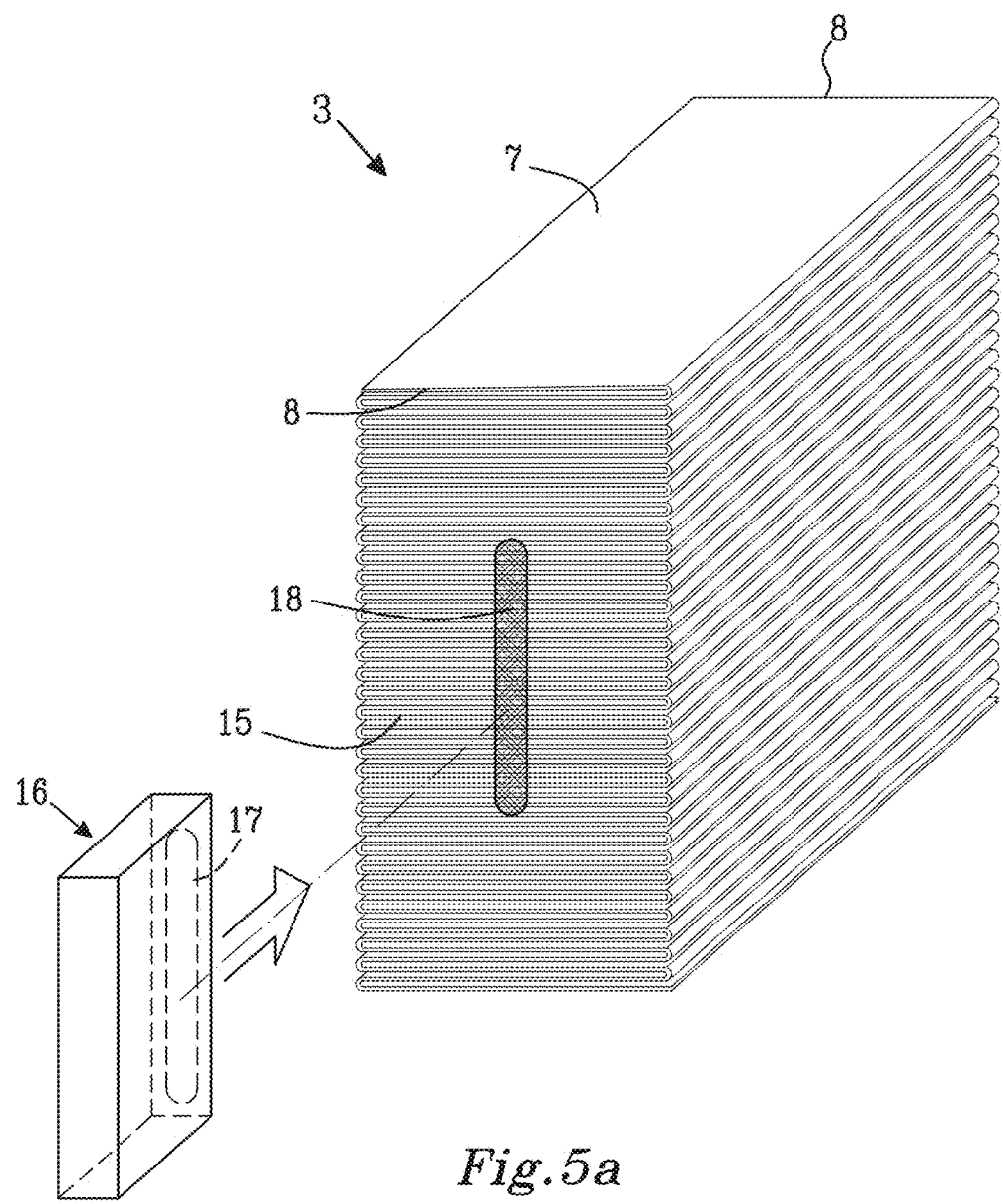
FIGS. 5a to 5d illustrate different methods for forming certain embodiments of stacks in accordance with the invention.
Figure 5B:
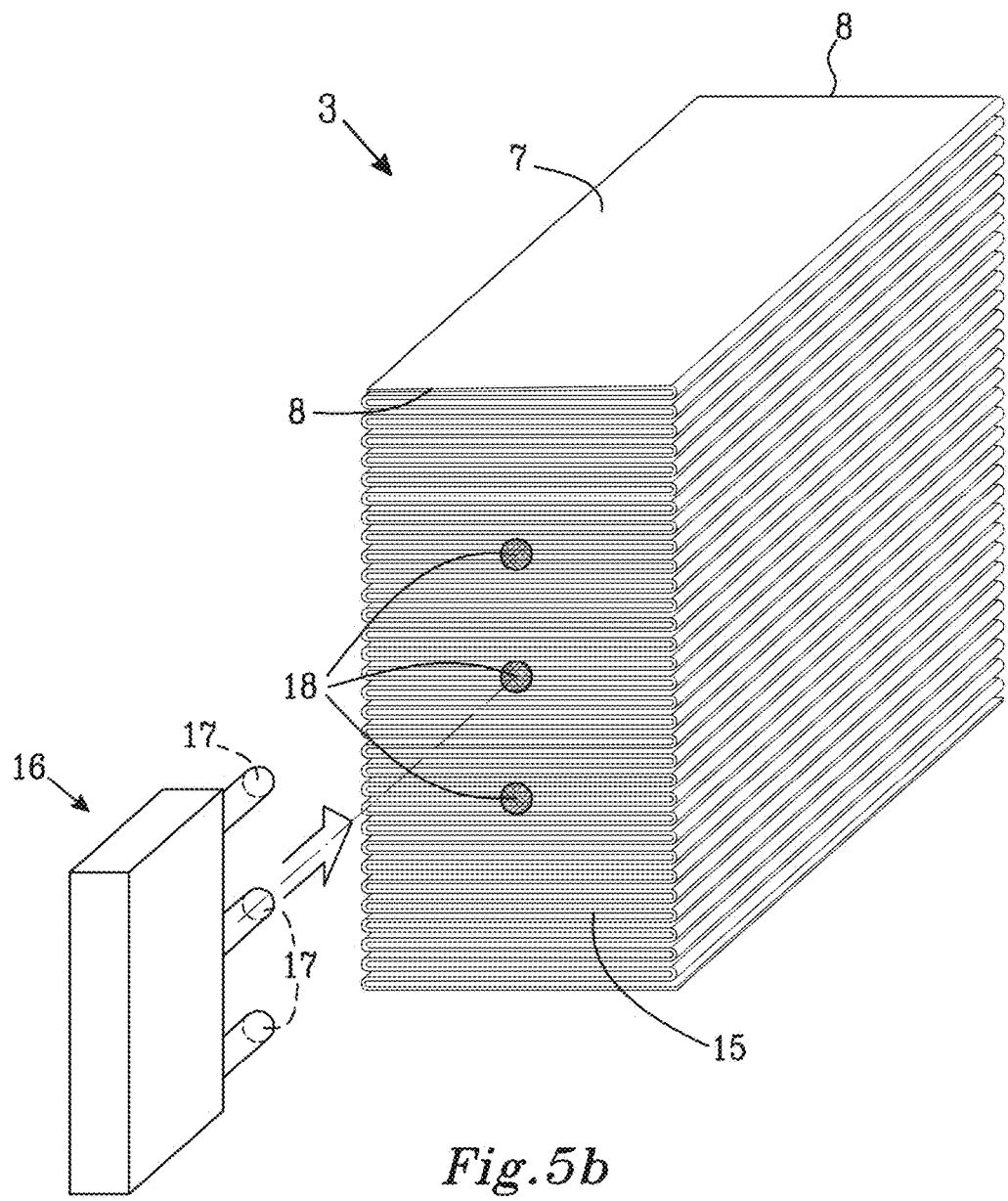
Figure 5C:
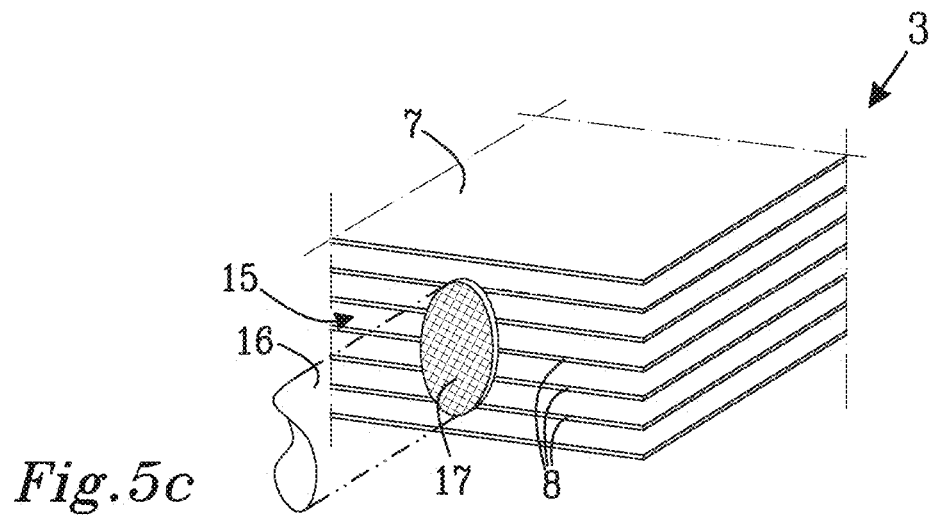
Figure 5D:
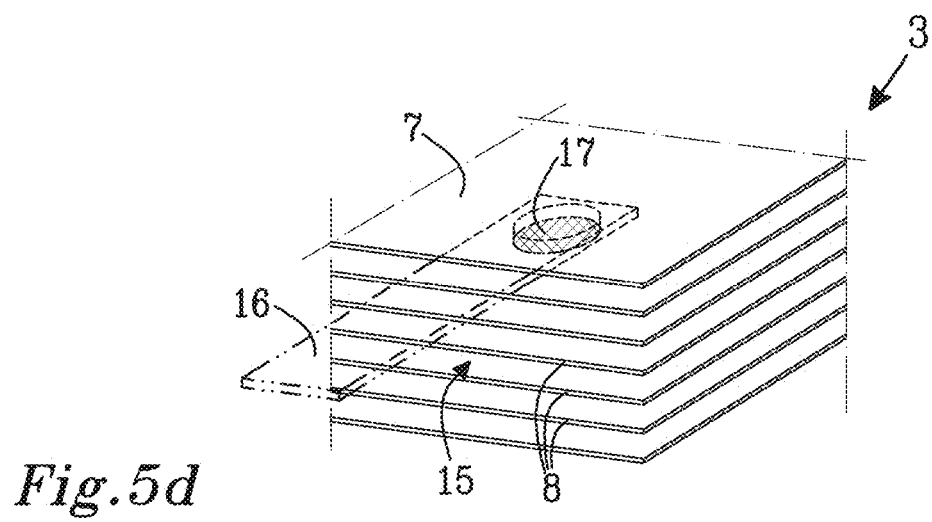

FIGS. 5a to 5c illustrate schematically embodiments of methods using a bar structure.

FIG. 5a illustrates a method using a smooth bar structure 16 having a straight edge 17. The edge 17 is provided with adhesive and then pressed towards the side 15 of the stack 3 (said side 15 comprising the longitudinal edge 8 of the webs). The result is an application site 18 forming a continuous line of adhesive running along the side 15 of the stack, over a length thereof corresponding to the length of the edge 17 of the bar 16. Such a line of adhesive will provide joint between the longitudinal ends of the two webs, as it will glue the edges 8 of the webs together where the edges are provided with glue. In this case, joints will be provided on every panel of the stack, meaning that the number of joints of each sheet will depend e.g. on how the sheets are folded into panels. Nevertheless, each individual sheet interconnection would, as defined in the above, comprise all joints interconnecting one specific sheets from each of the two webs. When the web material is unfolded (when the web material is fed from the stack), the continuous line of adhesive 18 will break into separate joints 5. Each such joint 5 will hold the two webs, together until a sheet adjacent the joint 5 is torn from the web material by the breaking of an adjacent weakening line.

FIG. 5b illustrates use of a serrated bar structure 16 whose edge has protrusions 17, which are provided with adhesive. The serrated bar structure 16 is pressed towards the side 15 of the stack 3, which results in a number of intermittent application sites 18 of adhesive. Depending on the size of the protrusions 17, the size of the intermittent application sites 18 may vary, from including a relatively large number of panels down to including only the edges 8 of the two webs, forming one panel. In the latter case, each intermittent application site 18 will form one single joint 5 between the two webs. In all other cases, each intermittent application site 18 will, when the web material is unfolded, break into several joints 5. The protrusions 17 could have a relatively small area, so as to form connections between few panels only, or to form only a single joint 5.

For forming joints 5 interconnecting the webs at the longitudinal edges 8 thereof, the serrated bar structure 16 should be arranged to press onto the end 5 of the stack 3, such that the protrusions 17 abut the longitudinal edges 8, as illustrated in FIG. 5c.

Optionally, a serrated bar structure 16 could be used for forming joints 5 interconnecting the webs 1,2, also via the web material surfaces 7 thereof. In this case, relatively small protrusions 17 are required. Such protrusions 17 may be introduced between the panels of the stack 3, instead of simply being pressed towards the side 15 of the stack. In this case, adhesive will be applied between the material surfaces 7 of the two webs, via a side of the stack 3.

The bar structures 16 described in the above could preferably have an elongate shape which is applied over the side 15 of the stack, either in a vertical direction as seen from a bottom and top of the stack, or in an inclined direction which extends at least in the vertical direction so as to provide joints distributed over the length of the webs.

However, one could also envisage a bar structure having a wider shape, e.g. being outlined by the width of the stack, for providing adhesive to selected positions anywhere over the end surface of the stack.

Alternatively, a rotating process or flexographic printing could be used to create the joints.

In view of the above, it will be understood that joints which are arranged to interconnect the longitudinal edges of said first and second web could be joints interconnecting both the longitudinal edges of the webs and the web material surfaces of the webs.

However, in a more preferred embodiment, the stack comprises at least some joints which are arranged to interconnect the longitudinal edges only of said first and second webs. In another preferred embodiment, the stack comprises substantially only joints which are arranged to interconnect the longitudinal edges only of said first and second webs.

With a joint being arranged to interconnect the longitudinal edges only of the first and second webs is meant a joint which primarily acts on said edges. For example, a dot of adhesive applied to the longitudinal edges would form such a joint. It will be understood that a small amount of adhesive might however penetrate a certain distance into the sheet from the edge, depending mainly on the viscosity of the adhesive and the absorption rate of the sheet material.

Naturally, joints may be created via one or both sides 15 of the stack 3.

Also, several joints may be applied to the longitudinal edges, and distributed over the panel width. In this case, each panel of the stack may be provided with a plurality of joints located at at least one of the longitudinal ends of the webs.

The frequency of individual sheet interconnections in the stack could be the subject for different considerations.

In many cases, it is a major concern to hinder the two webs from coming out of synchronization during dispensing from the stack. It has been found, that for this object to be achieved, it is sufficient that the stack contains relatively scarcely distributed individual sheet interconnections. Less than every fourth sheet need being interconnected, and in many instances even less than every $10^{th}$ every $20^{th}$ or less then $20^{th}$-$100^{th}$ sheet.

Which frequency is sufficient for a particular combination of web, separation strength of the individual sheet interconnection, and dispenser may be selected by some trial and error experiments by a skilled person, using the information disclosed herein as a starting point.

Indeed, when relatively few sheet interconnections are needed, one might choose to disregard the suggestion that the individual sheet interconnections shall have a separation strength being less than the separation strength of the weakening lines. This will indeed result in that, when an individual sheet interconnection is at hand, the user risks being served with two interconnected sheets. Usually, this is not a desired function. However, when this fault occurs relatively infrequently, it might be tolerated. This is particularly the case for frequencies of every $20^{th}$ sheet or more.

Naturally, a better option is to combine the teaching to use sheet interconnections with a frequency of less than every fourth sheet with the teaching that the sheet interconnections shall be weaker than the weakening lines.

Frequencies of every fourth sheet or more for the individual sheet interconnections may in particular be selected where there is a strong desire to facilitate re-threading of the web materials in a dispenser, in case an unintentional web brakeage should take place anywhere along the web. With such frequencies, strong individual sheet interconnections, that would result in two sheets (one from each web) becoming withdrawn at the same time at each individual sheet interconnection, usually cannot be tolerated. Hence, the separation strength of the individual sheet interconnections should be less than the separation strength of the weakening lines.

In the embodiment of FIG. 1, connection means 9 are provided at both ends of the stack 3. Such connection means 9 may be arranged at one or both ends of the stack and are intended to connect the stack to another, similar stack, so as to form a large, combined stack of material which may reside in the housing of a dispenser. Such large, combined stacks are formed so that a large amount of web material may be dispensed without need for refilling or rethreading of the dispenser.

Numerous types of connection means 9 are known in the art and may be used in the context of this application such as adhesive, adhesive initially covered with a protective foil, tapes, hook connections, hook and loop connections etc.

A connection means 9 for connecting the stack to another stack may be applied onto only one of the two webs. In this case, an individual sheet interconnection applied adjacent to the connection means 9 may be used to ensure that the other web will not lag behind when the web material is fed from the stack.

Alternatively, a connection means 9 may be applied so as to interconnect the two webs at the leading and/or trailing portion of the web material in the stack 3. Such an embodiment is depicted in FIG. 1, where one connection means 9 on the top side and one connection means 9 on the bottom side of the stack 3 interconnects the leading and trailing ends of the first and second web 1, 2, respectively.

It has been realized that, as a connection means interconnecting the first and the second web will indeed function so as to inhibit asynchronisation and/or facilitate threading of the web material in a dispenser, there is no need for joints forming individual sheet interconnections adjacent such connection means.

Hence, it is proposed herein to form a stack including a plurality of individual sheet interconnections, and where the leading and/or trailing portion of the webs are free from joints, the leading and/or trailing portion of the webs instead being provided with a connection means which interconnects the two webs.

The stacks as proposed herein may also advantageously be provided with a wrap for maintaining the shape of the stack during handling and storage thereof.

Figure 6:
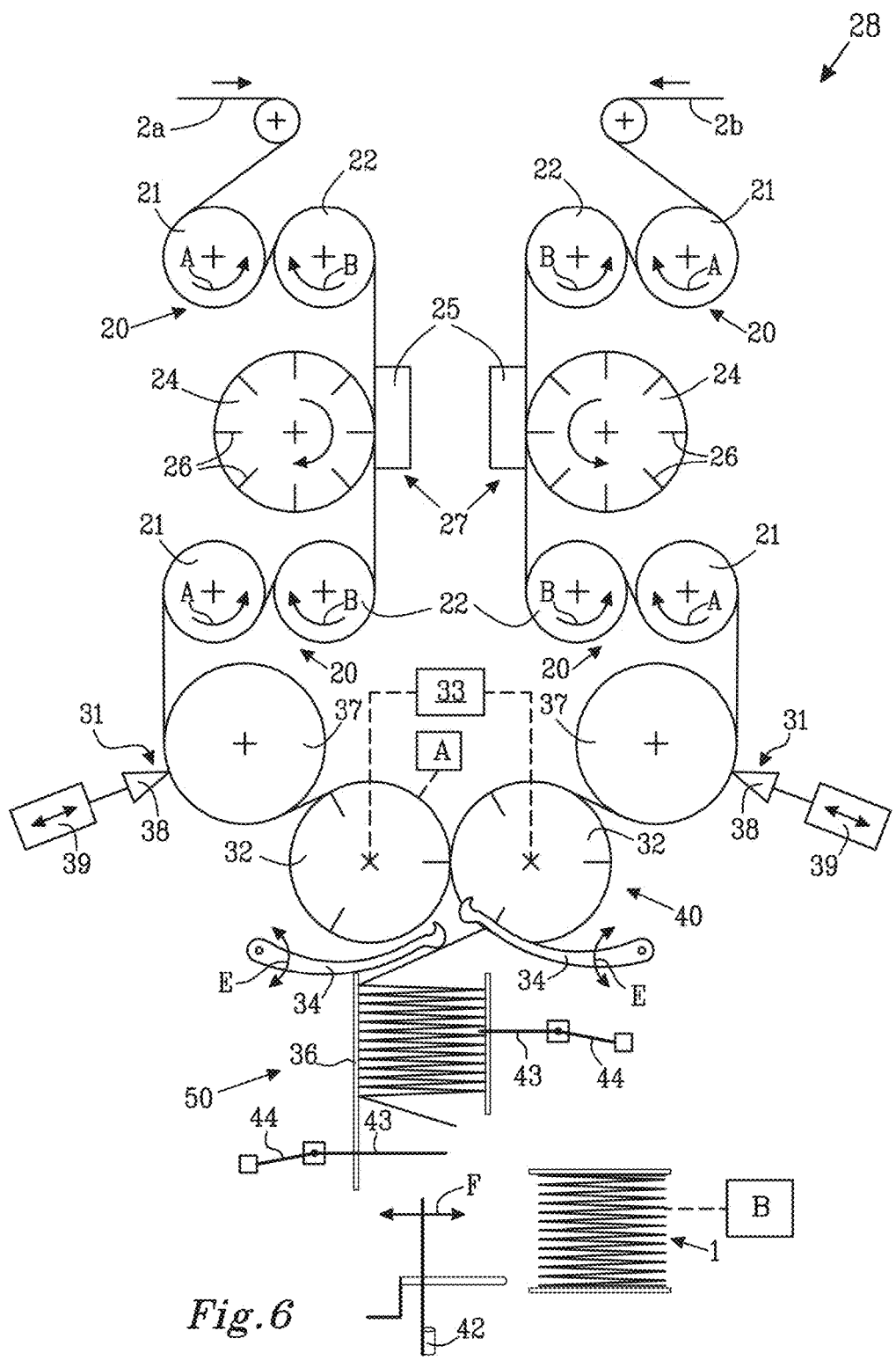
FIG. 6 illustrates a process for forming a stack in accordance with the invention.

FIG. 6 schematically shows the method and apparatus for producing a stack of interfolded sheets in accordance with some of the above-mentioned embodiments.

A first continuous web 2a and a second continuous web 2b are continuously conveyed to a first tensioning device 20, respectively. The first tensioning device consists of two rollers which are rotated in opposite directions A and B and around which the first web 2a and 20 second web 2b are wound in an S-shaped manner. There is a gap between the two rollers 21, 22 so that the webs 2a, 2b are not pinched in a nip between the two tensioning rollers. Due to the S-shaped contact of the webs around the rollers 21, 22, a high contact area between the web and the rollers is generated leading to a high friction between the webs and the rollers. In order to increase the friction, conventional methods can be applied like 25 varying the surface roughness of the circumferential surface of rollers 21, 22. A convenient way of increasing the friction is to cover the circumferential surfaces of the rollers with tungsten. Due to the friction between the webs 2a, 2b and the first tensioning device 20, the transport speed of the webs 2a, 2b is brought exactly to the circumferential speed of rollers 21, 22.

After leaving the first tensioning device 20, the webs 2a, 2b are directed to perforation stations 27 with perforation rollers 24 which act against anvil elements 25, respectively. The perforation rollers 24 are rotated at a circumferential speed which can be different to the transport speed of the webs 2a, 2b. The circumferential speed of the perforation rollers can be adjusted within a range of −60% and +40% relative to the conveying speed of the webs 2a, 2b.

The perforation rollers are provided with several perforation knives 26 which, according to this example, can be selectively activated or put in an idle state. This serves to use the device for various types of sheets consisting of two, three, four or even a higher number of panels for each sheet.

The perforation rollers generate perforation lines which run perpendicular to the length direction of the webs 2a, 2b. In order to avoid vibration of the perforation rollers, the time period of the perforation action can be extended by providing helical perforating elements to generate a continuously moving position at which a perforating element penetrates into the webs 2a, 2b.

Subsequent to the perforation rollers 24, there is a second tensioning device 20 which uses the same principle as explained above for the first tensioning device.

Although in this embodiment, equipment for forming perforation lines is used, it is understood that other types of equipment could be used for forming other types of weakening lines.

Preferably, the conveying speed of webs 2a, 2b at the second tensioning device is slightly higher than the conveying speed of the webs at the first tensioning device. The difference in speed can be up to 1%. This serves to tighten the web at the position at which the webs run through the perforating stations 27.

After leaving the second tensioning device, the webs 2a, 2b are directed to a cutting station 31 comprising anvil rollers 37 and cutting knives 38 which are functionally coupled to a suitable mechanism 39 which moves the cutting knife 38 in a reciprocating manner. When operated, the cutting knife 38 provides either a clean cut or a tab-bond so as to divide the webs 2a, 2b into individual web sections 2, 3.

In a first alternative of a method in accordance with the invention, a joint application station (A) is provided to apply joints in the form of adhesive to the webs 2a, 2b, after them being cut into individual web sections 2, 3. The joint application station (A) may advantageously comprise a spray application devise, providing adhesive to the web material surfaces of the web sections 2, 3.

The web sections are then transported to the vacuum folding device generally denoted by reference numeral 40. The mechanism 39 can be a cam mechanism or an electrically operated mechanism like a piezoelectric actuator.

When leaving the cutting station 31, the web sections 2, 3 are directed to a vacuum station 40 with vacuum folding rollers 32 which are connected to a device 33 generating sub-atmospheric pressure at parts of the circumference of the vacuum folding rollers 32.

This serves to make the webs alternately adhere to one of the two vacuum folding rollers which operatively cooperate with packer fingers 34 which are moved in the direction of arrows E and are used to separate the two web sections 2, 3 from the vacuum folding rolls 32 and to direct the folded web sections 2, 3 into the stacking station 50.

The stacking device 36 can be of any conventional type known to a skilled person. It is provided with a loader finger 42 adapted for a reciprocating movement in the direction of arrow F, separator fingers 43 moving upwards and downwards in the vertical stacking arrangement as shown in FIG. 3 and count fingers 44 which work together to count a predetermined number of folded sheets before the separator fingers cut off the web sections in case of still existing tab-bonds and before a finished stack is moved downwards and conveyed by loader finger 42 in the direction perpendicular to the stacking direction and away from the device.

In a second alternative of a method in accordance with the invention, the joint application station (B) is instead provided after the step of folding the web sections into stacks. The joint application station could again include a spray application device. However, in this case, the joint application station could suitably include a bar structure.

Different tensioning devices may be used to provide a tensioning of webs 2a, 2b and any variation of S-wraps around rollers and nips between rollers can be freely varied.

Although in the schematic representation in FIG. 6 a horizontal stacking machine has been shown, the key aspect of the invention can also be realized when using a horizontal stacking machine. It is the key aspect of the invention that besides the perforating device 27, a separate cutting device 31 is provided so that the position of the end edges of the top panels within one stack can be freely selected according to the specific needs of the user.

The perforation lines can be made mechanically strong enough, that is, with sufficient separation strength so that they are suitable to the intended use of the stack. In particular, they may be provided with sufficient separation strength so as to withstand the gravity force in an upwards dispensing dispenser with a considerable height of its supply magazine. Further, free selection can be made whether clear cuts or tap-bonds are realized in the cutting station since this operation is fully independent of the perforation step. When interfolding two web sections as shown in FIG. 5, the webs 2a, 2b are processed independently up to the folding rollers. Nevertheless, a central control unit is provided so that the perforation lines and clear cuts or tab-bonds can be adequately provided and positioned offset to each other in order to realize a stack as explained above with reference to FIG. 1.

Figure 7:
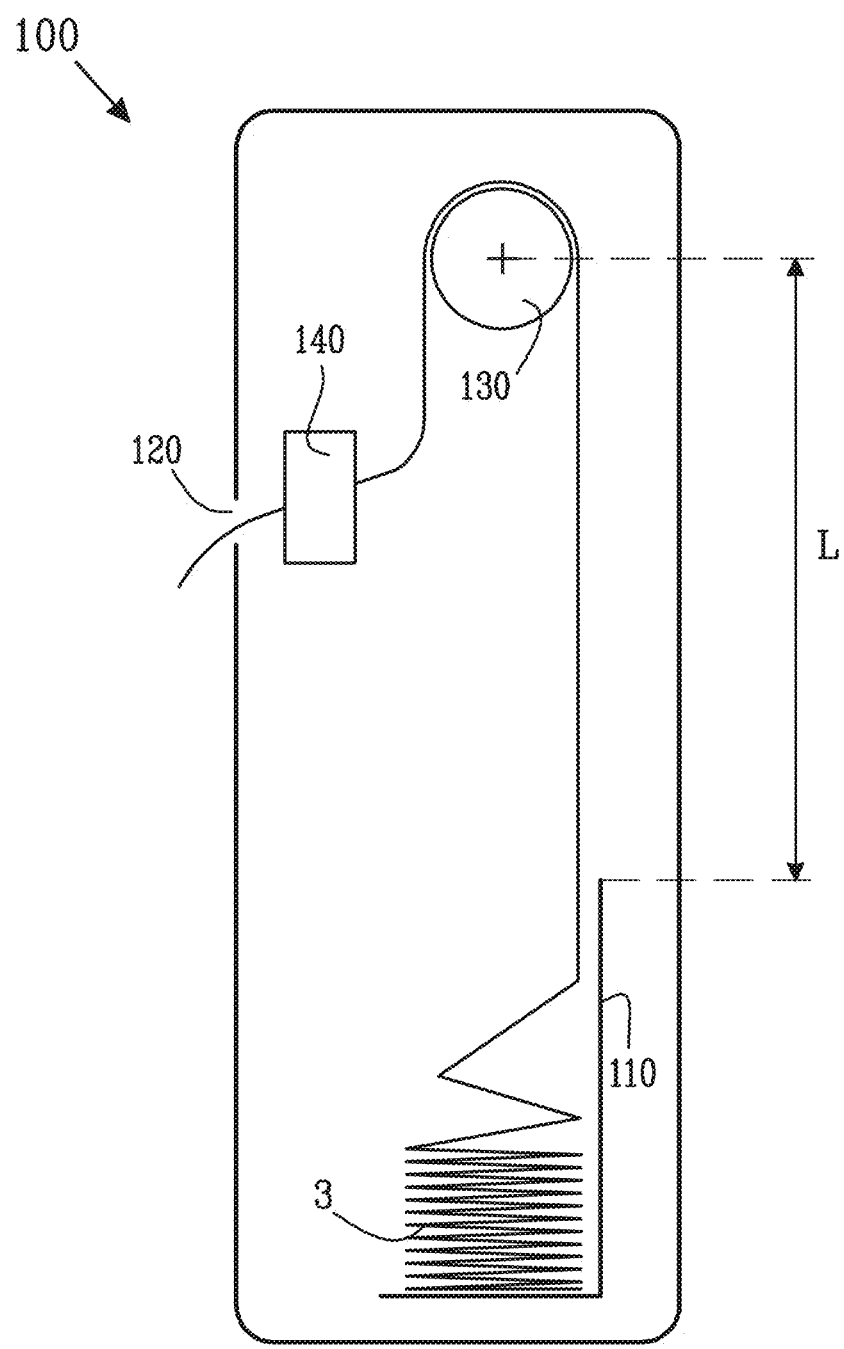
FIG. 7 illustrates a dispenser including a stack in accordance with the invention.

FIG. 7 illustrates an embodiment of a dispenser 100 including an embodiment of a stack 3 in accordance with the invention.

The dispenser 100 includes a storage space 110 containing the stack 3, from which web material is fed along a web path towards a dispensing opening 120. In the illustrated embodiment the web path is directed upwards from the storage space 110 towards a control unit 130, and then downwards towards a separation unit 140 arranged adjacent the dispensing opening 120.

The control unit 130 in this embodiment is designed to urge a slight pressure onto the web material. Accordingly, the control unit contributes to urging the first and the second web together, and is efficient to aid with maintaining synchronization of the webs. However, dispensers without such a control unit 130 could naturally also be used to dispense material from a stack 3 such as described herein.

The separation unit 140 is designed to separate the web material along the lines of weakness, when the leading end of the web material is pulled by a user.

Generally, the problem of the two webs becoming asynchronous during dispensing thereof, is particularly pronounced when the material is fed from the stack in a direction against the action of gravity, that is, when the material is fed from the top of the stack.

The stack could most easily be arranged in the dispenser in an upright position, that is, resting on a bottom panel of the stack only and extending in a vertical direction, such that web material may be fed from the top of the stack.

However, it may be envisaged that the stack is arranged in an inclined or even in a horizontal position, as long as one end panel of the stack (the "top") is free from carrying any weight of the stack, and the web material is fed from said end panel.

It will be understood, that the stack comprising individual sheet connections as suggested in accordance with the description above will greatly reduce the risk that the two webs become asynchronous during feeding thereof the web path of the dispenser.

Moreover, certain embodiments of stacks with relatively many individual sheet interconnections will also ensure that the web material may easily be rethreaded, even if a web breakage should occur somewhere along the web path.

Returning again to the issue considering the strengths involved in the dispensing of the stack, as an example it may be mentioned that for a dispenser of the type illustrated in FIG. 6, and intended for manual dispensing, the pulling force required for pulling a sheet from the dispenser is about 3-10N.

In a dispenser arranged for feeding of web material from the top of the stack, it is possible to achieve a close to constant withdrawal force when withdrawing the sheets from the dispenser, Moreover, the withdrawal force may be relatively low as seen in relation to other types of dispensers. For such a dispenser, a stack as described herein is believed to function particularly well. The separation strength of the lines of weakness of the stack may be in about the same range as the withdrawal force of the dispenser, for example about 1-30 N, preferably 3-20 N, most preferred 3-10 N.

As mentioned in the above, the separation strength of the individual sheet interconnections should be weaker than the separation strength of the separation strength of the lines of weakness, preferably considerably weaker. In this example, a separation strength of the individual sheet interconnections could hence be less than about 0.3-1 N.

However, naturally, the individual sheet interconnections must also have a sufficient strength so as to fulfill their purpose. By varying the amount of interconnections, distribution thereof, and strength thereof in a particular dispensing system, a person skilled in the art could find a suitable practical solution for that very system.

In view of the above, the person skilled in the art may clearly envisage several variants of the invention and adapt them to the needs of a specific situation.

Methods for Determining Separation Strengths

Strength of Individual Sheet Interconnections

Definitions:

Fax(N)—Maximum force recorded during testing

MD—Machine Direction

Sheet interconnection—the joints between two individual sheets, one from each web The maximum force separating the two sheets joined by the sheet interconnection is measured with a tensile strength tester.

Crosshead speed 50 mm/min

Clamp distance 100 mm 10N cell

Upper clamp with low weight

The width of the clamps may be selected to fit the samples.

Sample preparation:

Cut samples to the length of 150 mm. The width shall be adapted to include the entire sheet interconnection, with the sheet interconnection in the middle of the length direction. (One sheet will extend approximately 75 mm upwards from the connection, and the other sheet will extend approximately 75 mm downwards from the connection.)

Measure 10 samples in the machine direction.

The samples shall be conditioned for 4 h at 50±2% rh and 23±1° C., in accordance with ISO-187 standard.

Procedure

Prepare the tensile testing apparatus according to the apparatus instruction.

Adjust the length between the clamps to 100 mm and zero the equipment in the starting position.

Figure 8:
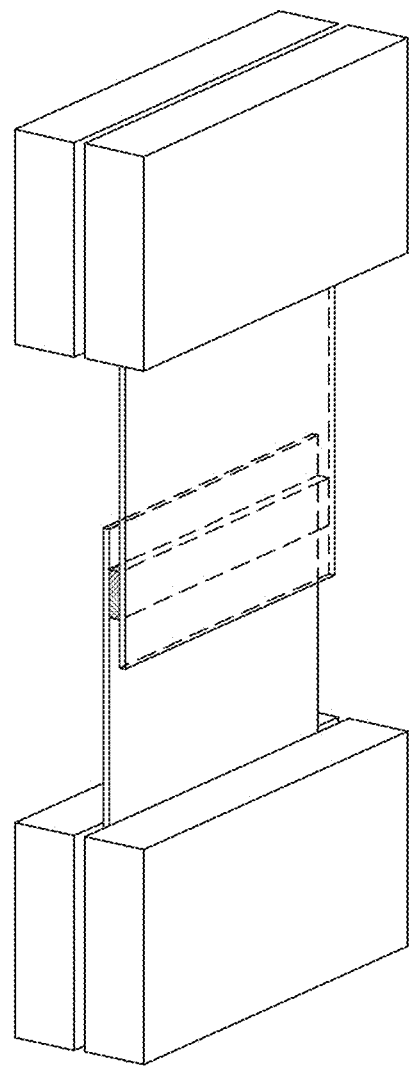
FIG. 8 illustrates the position of a sample when measuring separation strength.

Place the first sheet of the sample in the upper clamp and the second sheet in the lower clamp. The webs shall be sheared apart. See FIG. 8. (In FIG. 8, for the sake of better visibility, the size of the sheet interconnection has been greatly exaggerated.)

Start the tensile testing apparatus.

Repeat the test procedure for the remaining samples.

Calculation and Expression of Results

The software of the tensile strength tester records the highest peak detected during a test run for a sample. This maximum force (N) is used as a measure of the separation strength of the sheet interconnection of the sample. A mean value of the maximum force (N) of 10 samples is regarded as a representative value of the separation strength for the sheet interconnection of the samples N.B. The samples are to be similar, hence, they comprise similar web materials, and similar sheet interconnections. The resulting measure is to be representative of the selected combination of web materials and sheet interconnection.

Strength of Weakening Lines

Definitions:

Fax(N)—Maximum force recorded during testing

MD—Machine Direction

Linear strain—the material's elongation in per cent at the maximum force

The maximum force separating two individual sheets of a web, joined by a weakening line, is measured with a tensile strength tester.

Crosshead speed 50 mm/min

Clamp distance 100 mm 10N cell

Upper clamp with low weight

The width of the clamps may be selected to fit the samples.

Sample preparation:

Cut samples to the length of 150 mm, with the weakening line in the middle of the length direction. (One sheet will extend approximately 75 mm upwards from the weakening line, and the other sheet will extend approximately 75 mm downwards from the connection/weakening line. The width of the sample shall be the entire sheet width, and hence include the entire weakening line.

Measure 10 samples in the machine direction.

The samples shall be conditioned for 4 h at 50±2% rh and 23±1° C., in accordance with ISO-187 standard.

Procedure

Prepare the tensile testing apparatus according to the apparatus instruction.

Adjust the length between the clamps to 100 mm and zero the equipment in the starting position.

Place the sample between the upper and the lower clamp. Make sure that the sample is straight, and that the weakening line is in the middle between the clamps.

Start the tensile testing apparatus.

Repeat the test procedure for the remaining samples.

NB! Disregard samples which break elsewhere than along the perforation.

Calculation and Expression of Results

The software of the tensile strength tester records the highest peak detected during a test run for a sample. This maximum force (N) is used as a measure of the separation strength of the weakening line of the sample. A mean value of the maximum force (N) of 10 samples is regarded as a representative value of the separation strength of the weakening line of the samples.

N.B. The samples are to be similar, hence, they comprise similar web materials and weakening lines. The resulting measure is to be representative of the selected combination of web materials and weakening line.

Discussion Regarding Results

Various webs including perforation lines have been tested to determine useful separation strengths for such lines. For webs having basis weights 26-36 g/m2, a width of 212 mm, and perforation lines with a remaining bonded length being the total bond length/(total bond length+total slot length)of about 4-10%, separation strengths between 4-17 N have been measured.

As for individual sheet interconnections, tests have been performed on samples where glue in the form of a hot-melt adhesive, namely PVA adhesive with 4% dry content, has been applied in a line pattern to the longitudinal side of a stack including web material. The application was made using 90 mg of glue applied on an area with a length of 260 mm corresponding to the height of the stack, and a width of 5 mm. The glue was absorbed about 2 mm into the tissue material, resulting in an approximate size of the adhesive sheet interconnections between each panel of the stack of 2×5 mm.

For a stack as described above, and comprising Hybrid 2-ply web material, a mean separation strength of the individual sheet interconnections of 2.11 N was measured, with a standard deviation of 0.3 N.

For a stack as described above, comprising 1-ply TAD web material, a mean separation strength of the individual sheet interconnections of 1.8 N was measured, with a standard deviation of 0.3 N.

Accordingly, using the above methods, the separation strengths of the weakening lines and of the individual sheet interconnections may be determined with sufficient accuracy for the intended purposes.

Generally, a person skilled in the art may use his/her general knowledge about weakening lines and interconnections such as adhesive connections to adapt the parameters involved in order to arrive at desired separation strengths of the weakening lines and/or the sheet interconnections.

For creating the sheet interconnections of the stack used in the tests reported in the above, a method for applying adhesive to a web material was used wherein a serrated cylinder is arranged to rotate such that the serrated structure is dipped into a pool of adhesive. Upon rotation of the cylinder, the serrated structure is removed from the pool of adhesive, and brought towards the web material, Hence, the adhesive captured on the serrated structure is transferred to the web material. The web material may advantageously be moved linearly with a speed being adjusted to the rotation speed of the cylinder, such that continuous application of adhesive may be accomplished. Such a method may also be applicable in a large-scale method or apparatus for creating sheet interconnections between the two webs of a stack as described herein.

The invention claimed is:

1. Stack of folded web material for hygiene products, said stack comprising:
   at least two webs, the webs including:
   a first web divided into individual sheets by means of lines of weakness; and
   a second web divided into individual sheets by means of lines of weakness;
   said first and second webs being interfolded with one another so as to form said stack, and
      wherein the first web and the second web are arranged in said stack such that the lines of weakness of the first web and the lines of weakness of the second web are offset with respect to one another along the webs,
   each line of weakness having a separation strength, being the force required to separate an individual sheet from the web along said line of weakness,
   wherein
   the first web and the second web are joined to each other at a plurality of joints forming a plurality of individual sheet interconnections,
   wherein each individual sheet interconnection is formed by the joint or joints connecting an individual sheet of the first web with an individual sheet of the second web, and
   each individual sheet interconnection having a separation strength, being the force required to separate the two individual sheets of the first and the second web from each other, such that the joint or joints creating said individual sheet interconnection are broken, wherein
   the separation strength of the individual sheet interconnections is less than the separation strength of the lines of weakness.

2. Stack in accordance with claim 1, wherein the separation strength of the individual sheet interconnections is less than 0.9 times the separation strength of the lines of weakness.

3. Stack in accordance with claim 1, wherein the separation strength of the individual sheet interconnections is less than 0.1 times the separation strength of the lines of weakness.

4. Stack in accordance with claim 1, wherein the separation strength of the individual sheet interconnections is in the range 0.01-5 N.

5. Stack in accordance with claim 1, wherein the separation strength of the individual sheet interconnections is greater than 0.01 N.

6. Stack in accordance with claim 1, wherein the separation strength of the lines of weakness is in the range 1-30 N.

7. Stack in accordance with claim 1, wherein
   the joints of said individual sheet interconnections are formed by adhesive, and
   for each individual sheet interconnection, the amount of adhesive of the total joint or joints of said individual sheet interconnection is in the range 0.0001-1 mg, when calculated with a dry content of 100%.

8. Stack in accordance with claim 1, wherein each web defines a web material surface being delimited by longitudinal edges of the web, and the joints are formed so as to join the web material surface of the first web with the web material surface of the second web.

9. Stack accordance with claim 1, wherein the joints are formed from adhesive being applied in a dot pattern.

10. Stack in accordance with claim 1, wherein the joints are arranged to form a decorative pattern.

11. Stack in accordance with claim 1, wherein the joints comprise coloured adhesive for creating decorative effects.

12. Stack in accordance with claim 1, wherein each individual sheet interconnection comprises one joint only, said joint consisting of one dot of adhesive.

13. Stack in accordance with claim 1, wherein each web defines a web material surface being delimited by longitudinal edges of the web material, and the joints are arranged so as to interconnect the longitudinal edges of the first web with the longitudinal edges of the second web.

14. Stack in accordance with claim 13, wherein the joints are applied in an intermittent pattern as seen from a side of the bundle comprising said longitudinal edges.

15. Stack in accordance with claim 14, wherein each joint is formed by an amount of adhesive in the range 0.0001-1 mg.

16. Stack in accordance with claim 13, wherein the joints are applied in a continuous line pattern, as seen from a side of the stack comprising said longitudinal edges.

17. Stack in accordance with claim 1, wherein said stack comprises about 100 to 1000 individual sheets.

18. Stack in accordance with claim 1, wherein said lines of weakness of said first web are regularly distributed throughout the web, and the distance between consecutive lines of weaknesses corresponds to the length of the individual sheets, throughout the majority of the sheets of the stack.

19. Stack in accordance with claim 1, wherein said lines of weakness in said second web are regularly distributed throughout the second web, and the distance between consecutive lines of weaknesses corresponds to the length of the individual sheets.

20. Stack in accordance with claim 1, wherein the distance between consecutive lines of weakness in the first web is equal to the distance between consecutive lines of weakness in the second web.

21. Stack in accordance with claim 1, wherein the stack is provided with a connection means for connection to another stack at at least one of the ends of said stack.

22. Stack in accordance with claim 21, wherein the connection means comprises an adhesive, an adhesive pad, or a hook and loop/hook and hook fastener.

23. Stack in accordance with claim 1, wherein an individual sheet connection is provided at least on every fourth sheet throughout at least the majority of the length of the webs of the stack.

24. Stack in accordance with claim 1, wherein the individual sheet interconnections are distributed throughout the webs such that less than every fourth sheet of the webs are interconnected via individual sheet interconnections.

25. A dispenser including a housing having a storage space comprising web material in the form of a stack in accordance with claim 1,
   said dispenser having a dispensing opening for providing sheets of said web material to a user,
   said dispenser defining a web path, along which unfolded web material from said stack runs from said storage space to said dispensing opening, the storage space and web path being arranged such that web material is fed from the top of the stack.

* * * * *